United States Patent
Laurie et al.

(10) Patent No.: US 7,482,162 B2
(45) Date of Patent: Jan. 27, 2009

(54) DETERMINATION OF VITAMIN D METABOLITE AND DISPLACEMENT FROM PLASMA OR SERUM BINDING PROTEINS

(75) Inventors: David Laurie, Wylam (GB); Alexander Kirkley Barnes, Gateshead (GB); Michael James Gardner, Newcastle (GB)

(73) Assignee: Immunodiagnostic Systems Ltd. (GB)

( * ) Notice: Subject to any disclaimer, the term of this patent is extended or adjusted under 35 U.S.C. 154(b) by 0 days.

(21) Appl. No.: 10/433,923

(22) PCT Filed: Dec. 6, 2001

(86) PCT No.: PCT/GB01/05395

§ 371 (c)(1),
(2), (4) Date: Dec. 17, 2003

(87) PCT Pub. No.: WO02/46746

PCT Pub. Date: Jun. 13, 2002

(65) Prior Publication Data

US 2004/0096900 A1    May 20, 2004

(30) Foreign Application Priority Data

Dec. 6, 2000    (GB) ................. 0029729.1

(51) Int. Cl.
*G01N 33/49* (2006.01)
*G01N 33/02* (2006.01)
(52) U.S. Cl. .......... 436/20; 424/530; 424/531; 426/425; 426/429; 435/7.72; 435/7.9; 435/7.92; 435/188; 436/18; 436/71; 436/174; 436/177; 436/178; 436/817; 436/825; 436/826; 516/113; 516/139; 516/141; 516/143; 516/146; 516/153; 530/402; 530/412; 530/422; 530/423; 530/424

(58) Field of Classification Search ............ 435/4, 435/7.1, 7.5, 7.7–7.72, 7.92–7.95, 287.1, 435/287.2, 962, 975, 7.9, 28, 188; 436/71, 436/174–178, 817, 825, 517, 163, 18, 20, 436/826; 210/634, 635, 645, 646; 514/456, 514/822, 167, 168, 457; 549/400, 402, 423, 549/401; 568/327, 328; 424/530, 531; 426/425, 426/429; 516/113, 139, 141, 143, 146, 153; 530/402, 412, 422, 423, 424; 552/653

See application file for complete search history.

(56) References Cited

U.S. PATENT DOCUMENTS 1,735,142 A * 11/1929 Sugden .................. 8/440

(Continued)

FOREIGN PATENT DOCUMENTS

EP        0 982 592 A2    3/2000

(Continued)

OTHER PUBLICATIONS

Armbruster, FP. et al. Development of a novel ELISA for 1,25-dihydroxyvitamin D. Clin. Lab. 2000;46:165-166.*

(Continued)

*Primary Examiner*—Mark L Shibuya
*Assistant Examiner*—David J Venci
(74) *Attorney, Agent, or Firm*—K&L Gates LLP

(57) ABSTRACT

We disclose methods for measuring vitamin D metabolite in plasma or serum samples. The methods comprise a step of adding to the plasma or serum samples a non-competitive displacement agent comprising 8-anilino-1-naphthalene-sulfonic acid ammonium salt, 3-(acetonylbenzyl)-4-hydroxycoumarin and a water miscible solvent. The non-competitive displacement agent separates vitamin D metabolite from binding proteins in the sample, such that the displaced vitamin D metabolite is available for capture and detection in subsequent binding assays. Thus, our invention finds use in methods of separating and detecting vitamin D metabolites otherwise tightly bound to plasma or serum binding proteins.

12 Claims, 3 Drawing Sheets

U.S. PATENT DOCUMENTS

| | | | | |
|---|---|---|---|---|
| 2,427,578 | A | * | 9/1947 | Stahmann et al. ............ 549/286 |
| 3,955,925 | A | * | 5/1976 | Proksch et al. ................. 436/13 |
| 4,056,468 | A | * | 11/1977 | Breiter et al. ................ 210/672 |
| 4,366,143 | A | * | 12/1982 | Midgley et al. ............. 436/501 |
| 4,447,416 | A | * | 5/1984 | Menache-Aronson et al. ... 514/2 |
| 4,942,127 | A | * | 7/1990 | Wada et al. .................... 435/11 |
| 5,102,786 | A | * | 4/1992 | Cohen et al. .................. 435/7.9 |
| 5,112,956 | A | * | 5/1992 | Tang et al. ................... 530/424 |
| 5,232,836 | A | * | 8/1993 | Bouillon et al. ................. 435/8 |
| 5,332,662 | A | * | 7/1994 | Ullman ......................... 435/28 |
| 5,382,530 | A | * | 1/1995 | Romelli et al. .............. 436/500 |
| 5,395,755 | A | * | 3/1995 | Thorpe et al. ................. 435/28 |
| 5,501,956 | A | * | 3/1996 | Wada et al. ............... 205/777.5 |
| 5,532,138 | A | * | 7/1996 | Singh et al. ................. 435/7.93 |
| 5,821,020 | A | * | 10/1998 | Hollis .......................... 436/63 |
| 5,834,319 | A | * | 11/1998 | Ekins .......................... 436/518 |
| 6,468,757 | B2 | * | 10/2002 | Ramanathan et al. ......... 435/7.1 |
| 6,787,660 | B1 | * | 9/2004 | Armbruster et al. ......... 552/653 |
| 7,087,395 | B1 | * | 8/2006 | Garrity et al. .............. 435/7.93 |
| 2003/0185793 | A1 | * | 10/2003 | Kratz ......................... 424/85.1 |
| 2004/0132104 | A1 | * | 7/2004 | Sackrison et al. ............ 435/7.1 |

FOREIGN PATENT DOCUMENTS

| | | | |
|---|---|---|---|
| WO | WO 93/14405 | | 7/1993 |
| WO | WO 9821580 | * | 5/1998 |
| WO | WO 9967211 | * | 12/1999 |

OTHER PUBLICATIONS

Luque de Castro, MD. et al. Determination of vitamin D3 metablites: state-of-the-art and trends. J. Pharm. Biomed. Anal. 1999;20:1-17.*

Maggio, E.T. Enzyme-Immunoassay, Chapter 3, pp. 53-70, CRC Press, Inc. (1980).*

Thomas, W.C. et al. Studies of antiricketic activity in sera from patients with disorders of calcium metabolism and preliminary observations on the mode of transport of vitamin D in human serum. J. Clin. Invest. 1959;38:1978-1085.*

Jun, H.W. et al. Phenylbutazone-sodium warfarin binding using a fluorescent probe technique. J. Pharm. Sci. 1972;61:1835-1837.*

Ekins, R. The radioimmunoassay of free hormones in blood, in Free Hormones in Blood, pp. 73-90, Albertini, A. & Ekins, R.P., Eds., Elsevier Biomedical Press (1982).*

Price, P.A. & Sloper, S.A. Concurrent warfarin treatment further reduces bone mineral levels in 1,25-dihydroxyvitamin D3-treated rats, J. Biol. Chem. 1983;258:6004-6007.*

Yang, F. et al. Human group-specific component (Gc) is a member of the albumin family. Proc. Natl. Acad. Sci. USA. 1985;82:7994-7998.*

Matthews, J.C. Antagonism, in Fundamentals of Receptor, Enzyme, and Transport Kinetics, Chapter 8, pp. 63-94, CRC Press, Inc. (1993).*

Cholecalciferol, in the United States Pharmacopeia 24, National Formulary 19, pp. 404-405, United States Pharmacopeial Convention, Inc. (1999).*

Kosa, T. et al. Species differences of serum albumins: III. Analysis of structural characteristics and ligand binding properties during N-B transitions. Pharmaceut. Res. 1998;15:592-598.*

Moss, G.P. Nomenclature of fused and bridged fused ring systems. IUPAC Recommendations 1998. Pure & Appl. Chem. 1998;70:143-216. (p. 210 only).*

Hollis, B.W. Detection of vitamin D and its major metabolites, in Vitamin D, Chapter 38, pp. 587-606, Feldman, D., Glorieux, F.H. & Pike, J.W., Eds., Academic Press (1997).*

Epps, D.E. et al. A general, wide-range spectrofluorometric method for measuring the site-specific affinities of drugs toward human serum albumin. Anal. Biochem. 1995;227:342-350.*

Hollis, B.W. et al. Determination of vitamin D status by radioimmunoassay with an 125I-labeled tracer. Clin. Chem. 1993;39:529-533.*

Mackay, D. et al. Analysis of the binding of fluorescent ligands to soluble proteins. Use of simultaneous non-linear least squares regression to obtain estimates of binding parameters. Biochemical Pharmacol. 1991;41:2011-2018.*

Essassi, D. et al. Use of 1-anilino-8-naphthalene sulfonate as a fluorescent probe in the investigation of drug interactions with human alpha-1-acid glycoprotein and serum albumin. J. Pharmaceut. Sci. 1990;79:9-13.*

Sato, J. et al. Use of the fluorescence probe 1-anilino-8-naphthalenesulfonate in predicting interindividual differences in the plasma protein binding of acidic drugs in rats. J. Pharmaceut. Sci. 1984;73:519-524.*

Daiger, S.P. et al. Group-specific component (Gc) proteins bind vitamin D and 25-hydroxyvitamin D. Proc. Natl. Acad. Sci. USA. 1975;72:2076-2080.*

Sudlow, G. et al. The characterization of two specific drug binding sites on human serum albumin. Molec. Pharmacol. 1975;11:824-832.*

Belsey, R. et al. The physiologic significance of plasma transport of vitamin D and metabolites. Am. J. Med. 1974;57:50-56.*

Nilsson, S.F. et al. Binding of vitamin D to its human carrier plasma protein. Biochem. Biophys. Res. Commun. 1972;46:1380-1387.*

Vitamin D. assorted definitions, Stedman's Med. Dict. (27d), Mosby's Dental Dict. (2004), Acad. Press Dict. Sci. Tech. (1992), Am. Herit. Dict. Engl. Lang. (2007), Am. Herit. Med. Dict. (2007), Bender's Dict. Nutr. Food Tech. (2006), Chambers 21st Century Dict. (2001), Churchill Livingstone's Dict. Nursing (2006), Collins Engl. Dict. (2000), Collins Dict. Biol. (2005), Dict. Food (2005), Dict. Leisure Travel Tourism (2006), Mosby's Dict. Med. Nursing Health Prof. (2006), Penguin Engl. Dict. (2000), Dict. Med. (2000), Royal Soc. Med. (2002), (retrieved Oct. 21, 2008, mostly from <http://www.credoreference.com>). 20 printed pages.*

International Search Report, PCT/GB01/05395 (Immunodiagnostic Systems Ltd.).

Gardner et al., "A Direct, Non-Extraction Immunoassay for Measurement of 25-Hydroxyvitamin D," *J. of Bone and Mineral Res.*, (2001) 16(1): S434, Abstract Only.

Gardner et al., "Measurement of 25-Hydroxyvitamin D Using and Enzyme Immunoassay (EIA)," *J. of Bone and Mineral Res.*, (2000) 15(1): S456, Abstract Only.

Parsons et al., "Binding of Warfarin by Human Albumin in the Presence of a Perfluorochemical Blood Substitute," *Arch. Int. Pharmacodyn.*, (1985) 277: 4-14.

International Preliminary Examination Report, PCT/GB01/05395 ( Immunodiagnostic Systems Ltd.).

\* cited by examiner

DETERMINATION OF VITAMIN D METABOLITE AND DISPLACEMENT FROM PLASMA OR SERUM BINDING PROTEINS

CROSS-REFERENCE TO RELATED APPLICATIONS

This application was filed on Dec. 17, 2003, pursuant to 35 U.S.C. § 371, thereby obtaining priority to international application number PCT/GB01/05395, filed Dec. 6, 2001.

The present invention relates to a method for measuring the amount of a vitamin D metabolite present in a sample of plasma or serum, and in particular to a method which enables measurement of the amount of a vitamin D metabolite in a sample of plasma or serum without the need for prior extraction from the sample of vitamin D metabolite binding proteins. The present invention also relates to methods for determining the vitamin D status of a subject, for use in the diagnosis of disease, and to agents and kits for use in performing the methods of the invention.

Vitamin D status is an indication of the level of circulating vitamin D or vitamin D metabolites in a subject, and is an important factor in the cause of a number of diseases including rickets in children and osteomalcia in adults. It is also useful in identifying the underlying causes of hypocalcaemia and hypocalcaemia. Vitamin D and its metabolism are the subject of great clinical interest, and in line with this there has been a steady increase in the effort towards improving methods for the measurement of vitamin D and its metabolites in body fluids.

Vitamin D is available to man as either vitamin $D_2$ or vitamin $D_3$. Vitamin $D_2$ is produced outside the body by irradiation of ergosterol from yeast and fungi, and is found in man when taken in the form of fortified foods or pharmaceutical preparations. Vitamin $D_3$, on the other hand, is formed in animals from 7-dehydrocholesterol upon exposure to uv light. In man, this reaction occurs in the skin. Vitamin $D_3$ is also available in the diet, for example from fish liver oils. Vitamin D, in the form of vitamin $D_2$ or $D_3$, is rapidly converted to the circulating metabolite, 25-hydroxy vitamin D, which is found outside cells, tightly bound to circulating vitamin D binding protein (DBP). Due to the rapid conversion of vitamin D to its' metabolite, measurement of vitamin D does not give a useful indication of the vitamin D status of a subject. Other metabolites of vitamin D, such as 1α,25-dihydroxy vitamin D, circulate at a concentration 1000 times lower than non-1α-hydroxylated metabolites such as 25-hydroxy vitamin D, and so do not contribute significantly to the estimation of total circulating vitamin D metabolite. For this reason, the 1α-hydroxylated metabolites do not provide a direct or useful indication of vitamin D status. 25-hydroxy vitamin D is the metabolite with the highest serum concentration, and is easy to measure. It has therefore become the most common marker of vitamin D status in a subject.

The established methods for measurement of 25-hydroxy vitamin D provide a result which includes contributions from other vitamin D hydroxylated metabolites, principally 24,25-dihydroxy vitamin D but also 25,26-dihydroxy vitamin D and other metabolites. These other hydroxylated metabolites contribute 1 to 7% of the measure of total circulating vitamin D metabolites, the remainder being 25-hydroxy vitamin D. Whilst for many applications, including research, it is sufficient to measure the total amount of circulating vitamin D metabolites, for other applications separation of these metabolites is required to allow specific measurement of 25-hydroxy vitamin D. It is generally accepted that measurement of 25-hydroxy vitamin D levels in serum or plasma samples is the preferred method of determining the vitamin D status of a subject.

25-hydroxy vitamin D is found circulating in the serum or plasma, tightly bound to DBP (also known as Gc globulin). It is hydrophobic, and in addition to binding to DBP, it is found to bind strongly to other binding proteins such as albumin. The presence of such binding proteins, in particular DBP, presents a major difficulty in measuring serum or plasma levels of 25-hydroxy vitamin D.

To deal with this problem, methods for measurement of 25-hydroxy vitamin D to date have relied upon removal of DBP or other binding proteins from the sample to be analysed. This has typically involved an extraction step which separates the DBP from the vitamin D metabolite and removes the DBP from the sample, leaving behind the vitamin D metabolite. Extraction has been achieved by a number of methods, including solvent based extraction by adding to the sample an organic solvent such as chloroform, hexane or ethyl acetate and hexane. The organic and aqueous layers are separated and the solvent evaporated. The residue is then reconstituted in a water miscible solvent such as ethanol. Reverse phase cartridge extraction methods have also been used. Other traditional methods include the use of HPLC and chromatography to achieve separation of individual vitamin D metabolites and exclude from the sample interfering factors such as binding proteins.

Simplification of the methods for extraction and separation has been a key feature in the improvement of assays for vitamin D and its metabolites. For example, the chromatography step has been eliminated by the use of water miscible solvent such as acetonitrile to precipitate binding proteins. The binding proteins are then separated from the supernatant by centrifugation, and the supernatant is then analysed by immunoassay or competitive protein binding assay to determine the amount of vitamin D metabolite present.

While removal of vitamin D binding proteins from serum samples by organic solvents is effective, the process requires evaporation of volatile organic solvents which is not attractive for routine use in clinical biochemical laboratories. Although the use of water miscible solvents such as acetonitrile has largely eliminated the need for solvent evaporation, these have the disadvantage of being toxic. In addition, the requirement for a separate extraction step inevitably lengthens the assay time.

Boullion et al (Clin. Chem. 30/11 1731-1736 (1984)) describe "Two Direct (Non-Chromatographic) Assays for 25-Hydroxy Vitamin D". Whilst the assays described do not require a chromatography step as required in more traditional methods, they still require extraction of the vitamin D binding proteins from the sample by the use of solvent precipitation. Thus, the assays described in this publication suffer from the drawbacks mentioned above.

Holick et al (U.S. Pat. No. 5,981,779) describe methods for assaying vitamin D and its' metabolites in milk and other biological fluids. One of the solid phase assays described uses a competitive binding assay to measure the vitamin D metabolite in the sample, and comprises the steps of: (a) providing a solid phase support having immobilised thereon a protein or antibody which is capable of binding labelled vitamin D; (b) contacting the solid phase with a solution of labelled vitamin D to allow it to bind to the solid phase; (c) washing the solid phase to remove unbound labelled vitamin D; (d) contacting the solid phase with a sample suspected of containing vitamin D or its metabolite, for a time sufficient to displace the labelled compound; (e) collecting the liquid of (d); and (f) measuring the amount of labelled vitamin D in the liquid, which is proportional to the amount of vitamin D or metabolite in the test sample. This method is shown as a schematic in FIG. 3 ('779), when performed using milk as the test sample.

The method described is essentially a "free hormone" assay. In the example illustrated, the sample is milk which contains little DBP. The hydrophobic vitamin D will be bound to other milk proteins, the binding of which will be relatively low affinity compared with the binding for DBP. This is the basis on which a suitable competition between sample-derived vitamin D and labelled vitamin D tracer is achieved in the assay for milk samples. In samples containing significant amounts of DBP, for example serum, where the DBP level is ~400 mg/L, approximately 6% of the α-globulin fraction of serum, the "free" (i.e. that not bound to DBP) vitamin D is a very small proportion of the total (0.04% for serum). Such an assay is not suitable for measurement of vitamin D metabolite in these samples, a view which is further supported by Holick et al in a recent publication describing by a variation of the illustrated assay for application to serum samples. However, the only significant difference between the illustrated milk assay and the serum assay is the need for an additional solvent extraction stage to remove DBP and other proteins from the sample ($11^{th}$ Workshop on Vitamin D, 27 May-1 Jun. 2000, Nashville, USA). If serum was substituted for milk in the original assay, the labelled vitamin D originally bound to the DBP on the tube would simply equilibrate with the DBP present in the sample, of which 98% have unoccupied D binding sites. Such an assay would therefore only provide a measure of the capacity of the sample to bind a vitamin D-analogue, and not the sample's vitamin D content.

The Holick patent teaches that measurement of vitamin D (or metabolites) is possible in milk samples without need for an extraction process. It does not teach efficient methods by which the difficulties of vitamin D measurement in serum can be overcome.

Measurement of steroid hormones in serum, plasma or other biological fluids is carried out by a direct immunoassay, without the need for a separate extraction procedure. This has been achieved by the use of a steroid analogue which binds to the relevant steroid binding proteins, but does not cross react with the antibody used in the immunoassay. The steroid analogue saturates the steroid binding protein, displacing the steroid and allowing the steroid to bind to the antibodies of the immunoassay.

Use of a (specific) competitive displacer such as a vitamin D analogue that does not cross-react with the assay antibody, should be able to provide a "direct assay" (by analogy to direct steroid measurement methods). However there are two difficulties. Firstly, the concentration of DBP is very high in serum samples, typically ~400 mg/L (~7 μmol/l), and typically only ~2% of DBP has 25 hydroxy-vitamin D bound, the remaining ~98% DBP remains unoccupied and will bind potential competitive displacers. As a result the concentration of a specific competitive displacer must be sufficient to saturate the DBP and would need to be in excess if the affinity was lower than that of 25 hydroxyvitamin D. Vitamin D analogues are particularly expensive due to the complexity of vitamin D chemistry. Secondly, the specificity of DBP (for natural vitamin D metabolites) means that even with the availability of large numbers of different vitamin D analogues, very few have affinity for DBP that can compete with 25 hydroxyvitamin D.

The present invention aims to overcome or ameliorate the problems associated with the prior art, by providing an improved method for measuring vitamin D metabolite present in a sample of serum or plasma.

Thus, in a first aspect of the present invention there is provided a method for measuring vitamin D metabolite present in a plasma or serum sample of a subject, the method comprising:
(a) adding to a sample of serum or plasma a non-competitive displacement agent to effect separation of any vitamin D metabolite in the sample from protein to which it is bound, such that any vitamin D metabolite can be detected and/or measured; and
(b) detecting or measuring the amount of vitamin D metabolite in the sample of (a).

Thus, the present invention satisfies the pressing need for a simple yet effective method for measuring vitamin D metabolite in a serum or plasma sample. It is based upon the surprising discovery of non-competitive displacement agents which enable effective separation of vitamin D metabolites from binding proteins to enable the amount of vitamin D metabolites to be detected or measured, without competing with the protein or requiring its extraction from the sample. In essence, the invention provides for the first time displacement agents for use in vitamin D metabolite analysis which are not analogues or competitors of the vitamin D metabolites to be measured. The elimination of the need of both the extraction step and competitive displacement agents has enabled a method which is more efficient and cost effective than previous methods, and thus more suited to routine use in clinical biochemical laboratories or personal use.

The present invention may be performed on any sample of plasma or serum, preferably from a subject. The subject whose plasma or serum is to be analyzed may be one for whom it is desirable to determine vitamin D status. Preferably, the subject may be a mammal. More preferably, the subject is a human, and most preferably a child.

Measuring vitamin D metabolite present in a sample of plasma or serum may include both detecting the presence of any vitamin D metabolite in the sample, or more preferably, determining the amount of vitamin D metabolite present. The amount may be compared with a key detailing whether the amount represents a deficiency or excess of vitamin D metabolite.

Any one or more metabolites of vitamin D may be measured in the method of the present invention. In a preferred embodiment, a specific vitamin D metabolite is measured in a sample, although it is envisaged that for some applications it may be preferred to measure two or more types of metabolite present. Examples of metabolites include 25-hydroxy vitamin $D_2$, 25-hydroxy vitamin $D_3$, 24,25-dihydroxy vitamin $D_3$ and 25,26-dihydroxy vitamin D. 25-hydroxy vitamins $D_2$ or $D_3$, or analogues thereof, are the preferred metabolites to be measured in the method of the invention.

The method of the invention is not restricted to the separation, or displacement, of a vitamin D metabolite from DBP, but may be used in the separation of a vitamin D metabolite from any factor to which it is bound. Typically, such factors will be proteins, for example, serum albumin.

By displacement is meant full or partial separation of some or all of the vitamin D metabolite from the factor to which it is bound in the sample. Preferably, the displacement of the vitamin D metabolite from the binding factor is sufficient to enable the vitamin D metabolite to detected and/or measured, for example in a binding assay. It is preferred that substantially all of the vitamin D metabolite present in the sample is sufficiently displaced from the binding factor, to enable it to be measured. In this context, "substantially" means at least 95%, 98% and preferably at least 99% of the vitamin D metabolite is displaced. This ensures accuracy of a test based upon the method of the invention.

Any non-competitive agent capable of achieving displacement, or separation, of the vitamin D metabolite from the binding protein may be used in step (a) of the method of the invention. Preferred agents for use in the present invention are chemical reagents which may act by disrupting or destroying the bond between vitamin D metabolite and binding factor. Preferred chemical reagents for use as displacement agents are those which bind to vitamin D binding proteins such as albumin with sufficient affinity to assist displacement of the vitamin D metabolite. In a most preferred embodiment of the present invention, the displacement agent is a chemical reagent comprising, preferably in a buffer, 8-anilino-1-napthalenesulphonic acid ammonium salt, 3-(acetonylbenzyl)-4-hydroxycoumarin and a water miscible solvent. Any suitable buffer may be used, for example phosphate buffered saline. Suitable water miscible solvents will be known to persons skilled in the art and include ethanol, acetonitrile, propan-1-ol, propan-2-ol, acetone, dimethylformamide and methyl sulphoxide. The preferred water miscible solvent is methanol. The suitable concentrations and proportions of the three reagents for producing the displacement agent can be readily ascertained by persons skilled in the art. Preferred concentrations of the reagents are 0.5 to 10 g/l, more preferably 1.60 g/l 8-anilino-1-napthalenesulponoc acid ammonium salt; 50 to 1000 mg/l, and more preferably 160 mg/l 3-(acetylonylbenzyl)-4-hydroxycoumarin and 10 to 300 ml/l, more preferably 160 ml/l water miscible solvent such as methanol.

Once the vitamin D metabolite has been displaced from the binding factor in the sample, the presence or amount of vitamin D metabolite in the sample may be determined. Any suitable method may be used for this purpose, and such methods will be familiar to persons skilled in the art. Examples of suitable methods include binding assays, such as competitive or non-competitive binding assays, immunoassays, or direct labeling of unbound vitamin D metabolites.

The step (b) of measuring the amount of vitamin D metabolite in the sample may be performed subsequent to, or simultaneously with step (a). Preferably, the step (b) is carried out simultaneously with step (a), thus providing a single step assay or measurement of vitamin D metabolite in a serum or plasma sample.

One of the preferred methods for measuring displaced vitamin D metabolite in a sample is by way of a competitive binding assay. Suitable competitive binding assays take various forms, and will be well known to persons skilled in the art. A typical competitive binding assay will comprise contacting a receptor with a labeled form of a ligand and a sample suspected of containing an unlabelled form of the same ligand. The amount of labeled ligand which is found bound to the receptor is indicative of the proportion of unlabeled ligand in the sample. Alternatively, the competitive binding assay may comprise providing receptors bound to a labeled form of the ligand, adding to the receptors the sample suspected of containing the unlabelled form of the ligand, and measuring the amount of displaced labeled ligand which is indicative of the amount of unlabelled ligand present.

In a preferred embodiment of the first aspect of the invention, there is provided a method of measuring the amount of displaced vitamin D metabolite in a sample, comprising the steps of:
(a) providing a support having immobilised thereon a binding factor capable of binding a vitamin D metabolite;
(b) contacting the support with a sample comprising the vitamin D metabolite to be measured;
(c) contacting the support with a labeled form of the vitamin D metabolite;
(d) measuring the amount of labeled vitamin D metabolite left bound to the support, wherein the amount of labeled vitamin D metabolite bound to the support is proportional to the amount of vitamin D metabolite in the sample.

Where it is preferred to perform the binding assay simultaneously with the displacement step, the method of the first aspect may comprise the steps of
(a) providing a support having immobilised thereon a binding factor capsule of binding a vitamin D metabolite;
(b) contacting the support with a serum or plasma sample of a subject;
(c) adding to the support a non-competitive displacement agent to effect separation of the vitamin D metabolite from protein to which it is bound;
(d) contacting the support with a labelled form of the vitamin D metabolite;
(e) measuring the amount of labelled vitamin D metabolite left bound to the support;

wherein the amount of labelled vitamin D metabolite bound to the support is proportional to the amount of vitamin D metabolite in the sample.

The binding factor to be immobilized on the support may be any factor capable of binding a labelled or unlabelled form of the vitamin D metabolite. The binding factor may a protein, such as albumin or DBP, or an antibody specific for the particular vitamin D metabolite of interest. In a most preferred embodiment, the binding factor is an antibody against the vitamin D metabolite. Preferably, the antibody is polyclonal.

In an alternative embodiment, the vitamin D metabolite may be measured by way of an immunoassay. Any suitable form of immunoassay may be used, and these will be known to persons skilled in the art. For example, the displaced vitamin D may be captured on a support of vitamin D metabolite specific antibodies, and then quantified using a second, labeled vitamin D metabolite specific antibody.

Any suitable labeling means may be used in the above methods. Suitable labels include enzymatic labels, such as alkaline phosphatase, peroxidase, biotin-streptavidin, fluorescent labels such as flourescin or rhodamine, or chemiluminescent labels such asluminol, acridium esters, and 1,2-dioxetanes. Also included are combinations of the above, for example avidin-fluorescin, as an alternative for avidin-HRP.

In a second aspect of the invention, there is provided a method for determining the vitamin D status of a subject, the method comprising:
(a) adding to a sample of serum or plasma a non-competitive displacement agent to effect separation of any vitamin D metabolite in the sample from protein to which it is bound, to produce a sample comprising unbound vitamin D metabolite and protein; and
(b) measuring the amount of vitamin D metabolite in the sample of (a).

The vitamin D status of a subject is highly informative, and may be used to determine the underlying cause of a number of disease states including rickets, and hyper- or hypo-calceamia. Thus, in a preferred embodiment of the second aspect of the invention, the method relates to determining the cause of disease in a subject, wherein preferably, the subject is a human and most preferably a child.

The present invention is performed in vitro, on a sample of serum or plasma removed from a subject. Thus, preferably, the method comprises the additional step of first removing a serum or plasma sample from the subject. The present invention therefore relates to a non-invasive method, the results of which may be used in a determining vitamin D status of a subject, and thus the underlying to disease. The method does not however provide a result upon which an immediate medical decision regarding treatment must be made.

In a third aspect of the present invention, there is provided a displacement agent as defined in relation to the first aspect.

In a fourth aspect of the invention, there is provided the use of an agent of the third aspect. In a method for measuring vitamin D metabolite in a sample of serum or plasma, or for determining the vitamin D status of a subject, preferably the displacement agents are used in methods of the first and second aspects of the invention.

In a fifth aspect of the invention, there is provided a kit for use in a method of the first or second aspects, comprising a displacement agent according to the second aspect of the invention. The kit preferably also comprises a key showing the correlation between the results of the assay with the amount of vitamin D metabolite present in the sample. In a further preferred embodiment, a kit may comprise means for carrying out step (b) of the first aspect of the invention. Such means may include one or more of a support, labelled vitamin D metabolites, antibodies, proteins on labels. The kit preferably will also comprise instructions for use.

The preferred embodiments apply to each aspect, *mutatis mutandis*.

The present invention will now be described by way of a non-limiting example, with reference to the following figures, in which.

EXAMPLE

Figure 1:
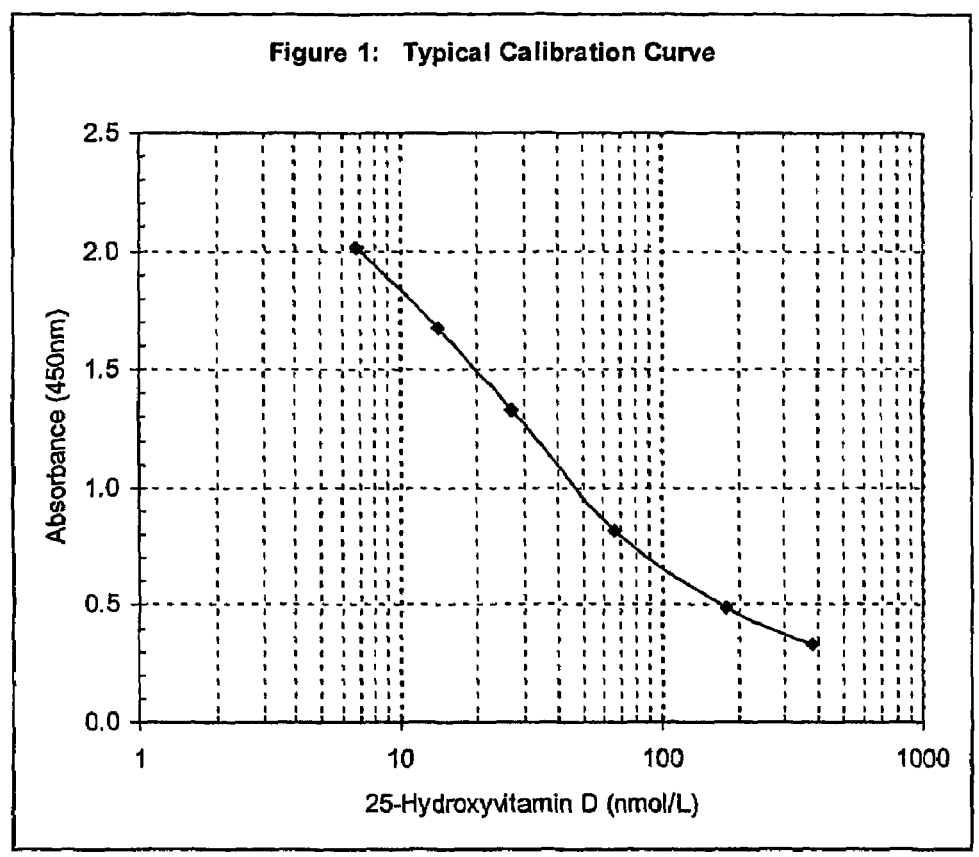
FIG. 1 shows a typical calibration curve for the direct 25-hydroxyvitamin D enzyme immunoassay.

Preparation of Anti-Vitamin D Coated Microtitre Plates

Donkey anti-(sheep IgG) serum and sheep anti-vitamin D were both purified by sodium sulphate precipitation to give the corresponding IgG fractions. Microtitre plates (Nunc Maxisorp) were coated with donkey anti(sheep IgG), a purified IgG, 250 μl per well of 30 mg/l IgG in 10 mM phosphate buffered saline (PBS) and incubated overnight at room temperature. The coated plates were washed three times with 10 mM phosphate buffered saline, 0.05% Tween 20(PBST). Sheep anti-vitamin IgG, 1 ng/ml in PBS, 0.1% Polypep (Sigma), 0.05% sodium azide, 200 μl per well was added and plates stored at 2-8C. Plates were washed with PBST before use.

Preparation of Vitamin D Biotin

A solution of 24,25-dihydroxyvitamin D in methanol (200 μl/mg/mL) was treated with an excess of sodium periodate in water for 1 hour at room temperature and purified by HPLC chromatography (Hypersil C18 column 4.6 mm×125 mm, 50% methanol/water, elution gradient of 50% to 100% methanol). The eluted fractions containing (25,26,27-nor)-vitamin D-24-aldehyde were treated with excess carboxymethyl oxime (Sigma) methanol for 4 hours, purified by HPLC chromatography (as above) to provide 24-CMO-vitamin D. The N-hydroxysuccinimide ester was prepared by treatment of 24-CMO-vitamin D with excess N-hydroxysuccinimide and dicyclohexylcarbodiimide in dioxan. The N-hydroxisuccinimide ester of 24-CMO-vitamin D and biotin N-hydroxysuccinimide ester (Sigma) were added to bisaminopolyethylene glycol (Sigma) in dioxan solution and allowed to react for 3 hours at room temperature. Excess 24-CMO-vitamin D and biotin were removed by dialysis and the vitamin D-biotin conjugate was stored at −20C.

Vitamin D Displacement Agent

The preferred formulation of the vitamin D displacement agent is any conventional buffer, such as phosphate buffered saline solution containing 8-anilino-1-napthalenesulphonic acid ammonium salt (0.5 to 10 g/l, preferably 1.6 g/l), 3-(α-acetonylbenzyl)-4-hydroxycoumarin (50 to 1000 mg/l, preferable 160 mg/l) and methanol (10 to 300 ml/l, preferably 160 ml/l.

Enzymeimmunoassay

A typical assay procedure is as follows:

A portion of sample (25 μl serum or plasma) is diluted with 1 ml of vitamin D displacement agent as described above. A portion of the diluted sample (100 μl) is added to the anti-vitamin D antibody coated microtitre plate, followed by addition of a solution (100 μl) of the vitamin D-biotin conjugate, and incubated for 90 minutes at room temperature. The plate was washed three times with 10 mM phosphate buffered saline containing 0.05% Tween20 (PBST). Avidin peroxidase conjugate (Sigma) diluted 1:2000 in PBST was added and incubated for 30 minutes at room temperature, followed by washing three times with PBST. TMB (tetramethylbenzidine) substrate reagent (Moss Inc.) was added and colour allowed to develop for 30 minutes. After addition of 0.5M HCL to stop the reaction, the absorbance was recorded at 450 nm.

A calibration curve is prepared with each batch of samples being analysed, and the 25-hydroxyvitamin D values for each sample can be read directly from the calibration curve using the absorbance value obtained for each sample. This can be performed manually from a calibration curve plotted on graph paper, or more usually by suitable data processing software.

A typical calibration curve for the direct 25-hydroxyvitamin D enzymeimmunoassay is shown in FIG. 1.

| 25-Hydroxyvitamin D (nmol/L) | Absorbance at 450 nm | B/Bo (%) |
|---|---|---|
| 0 | 2.436 | 100% |
| 6.8 | 2.015 | 83% |
| 14 | 1.678 | 69% |
| 27 | 1.330 | 55% |
| 67 | 0.815 | 33% |
| 179 | 0.484 | 20% |
| 380 | 0.332 | 14% |

Figure 2:
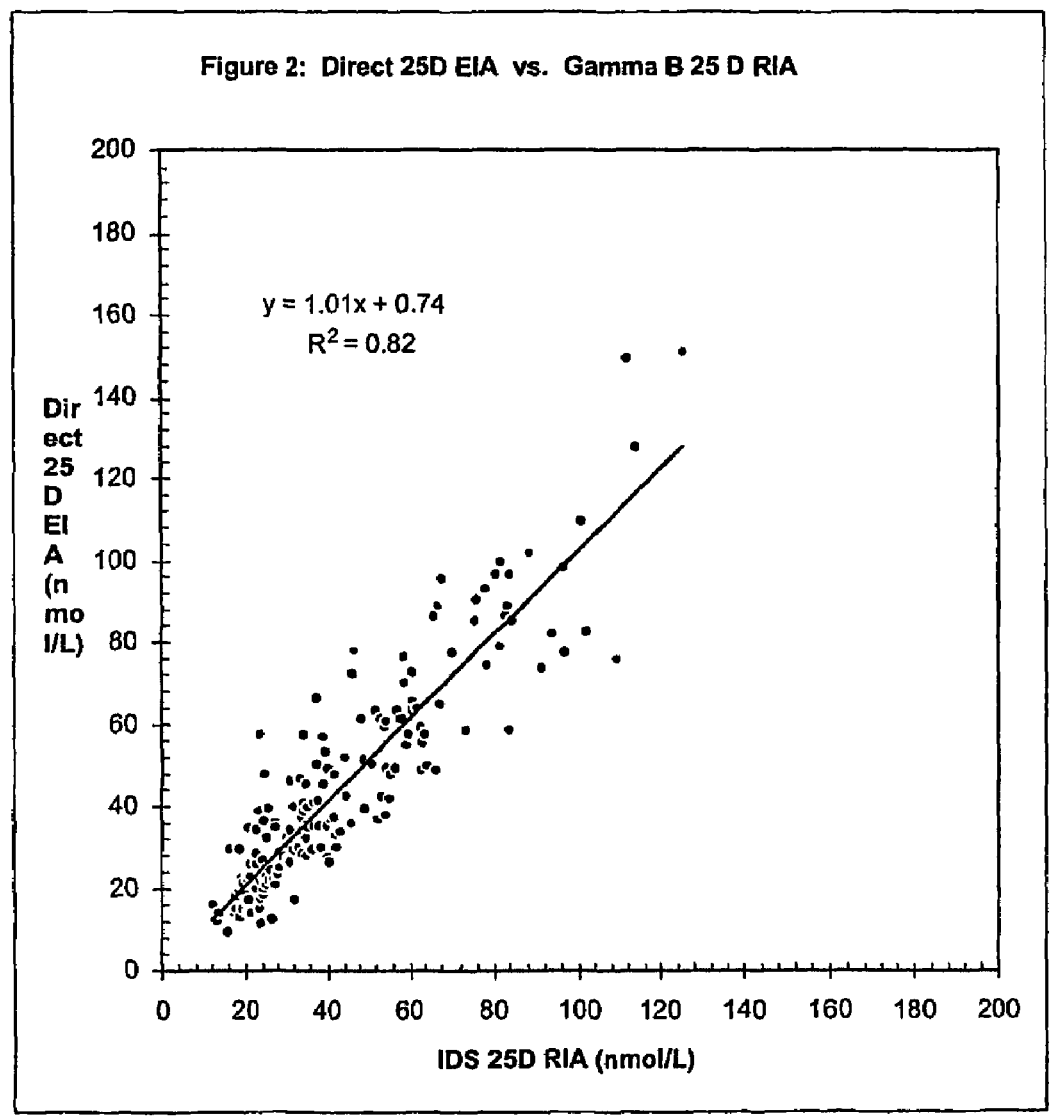
FIG. 2 shows a correlation of the direct enzyme immunoassay of the present invention with Immunodiagnostic Systems Ltds' Gamma B 25-Hydroxy Vitamin D radioimmunoassay (IDS catalogue number AA-35F1) with 180 serum or plasma patient samples.
Figure 3:
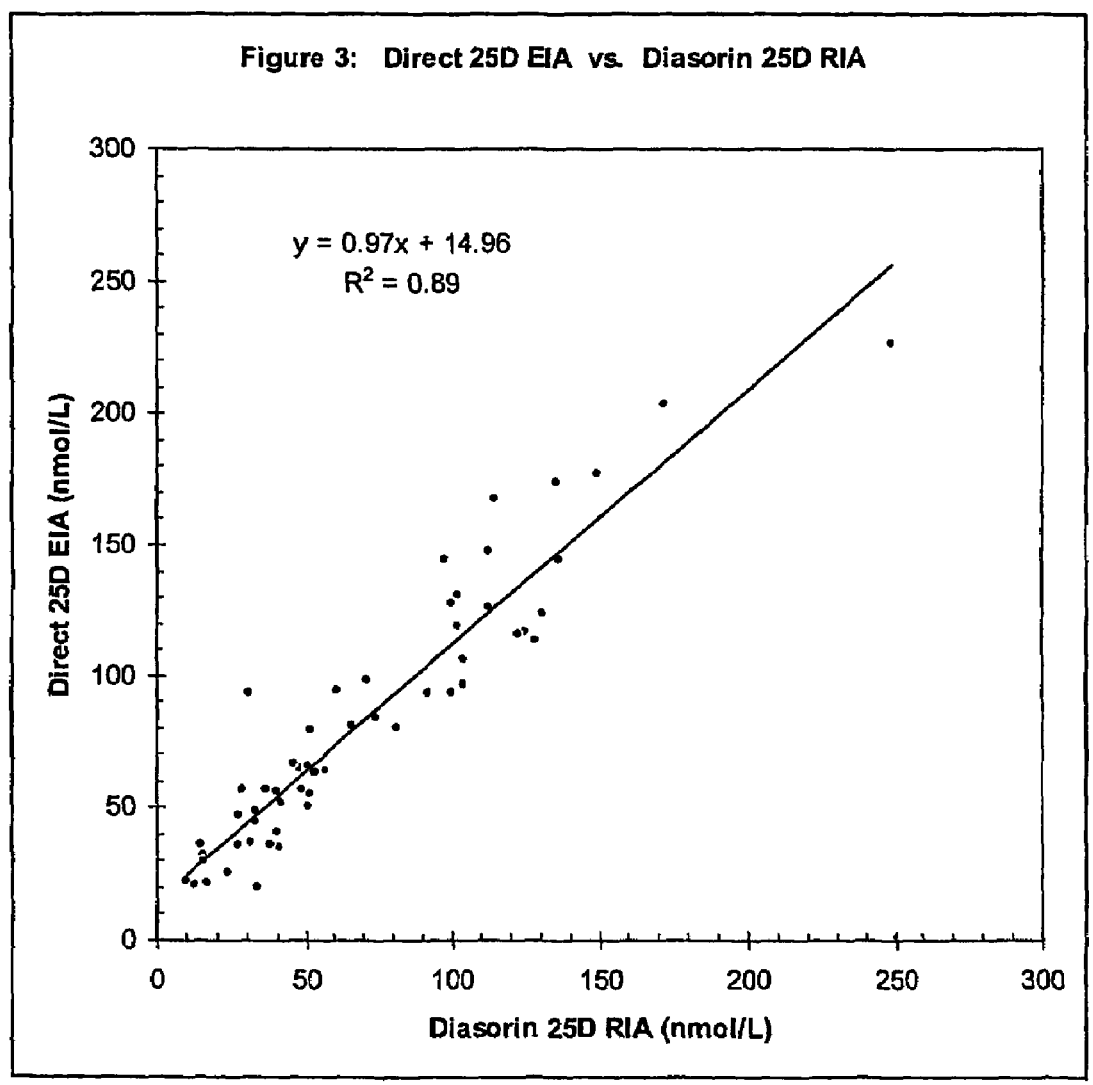
FIG. 3 shows a correlation of the direct enzyme immunoassay with the Diasorn 25-Hydroxy Vitamin D $^{125}$I RIA (catalogue number 68100E, Diasorin, Stillwater, Minn., USA) with 55 serum or plasma patient samples

To demonstrate effectiveness of the direct 25-hydroxyvitamin D enzymeimmunoassay with patient samples, the assay was compared to two commercially available radioimmunoassays, both of which use an extraction step as part of sample preparation prior to assay. The two radioimmunoassays are widely used clinically for the quantitative determination of 25-hydroxyvitamin D and other metabolites in human serum or plasma as part of the assessment of vitamin D sufficiency. The direct 25D enzymeimmunoassay shows good agreement and correlation with two established extraction radioimmunoassys, thus demonstrating the utility of a direct 25-hydroxyvitamin D enzymeimmunoassay for the quantitative determination of 25-hydroxyvitamin D (and other metabolites) in serum or plasma specimens (FIGS. 2 and 3).

The invention claimed is:

1. A method for measuring vitamin D metabolite present in a plasma or serum sample, the method comprising:
   (a) adding to a serum or plasma sample a non-competitive displacement agent comprising 8-anilino-1-napthalenesulfonic acid ammonium salt, 3-(acetonylbenzyl)-4-hydroxycoumarin and a water miscible solvent, which separates any vitamin D metabolite in the sample from protein to which the vitamin D metabolite is bound, such that any separated vitamin D metabolite can be captured;
   (b) contacting the sample with a support having immobilised thereon a binding factor, the binding factor capturing any vitamin D metabolite separated in step (a); and
   (c) measuring the amount of vitamin D metabolite captured in step (b);
   wherein capture of separated vitamin D metabolite occurs in step (b) without prior extraction from the sample of the protein separated from the vitamin D metabolite in step (a).

2. The method of claim 1, wherein the vitamin D metabolite is 25-hydroxy vitamin D.

3. A method for measuring vitamin D metabolite present in a plasma or serum sample, the method comprising:
   (a) adding to a serum or plasma sample a non-competitive displacement agent comprising 8-anilino-1-napthalenesulfonic acid ammonium salt, 3-(acetonylbenzyl)-4-hydroxycoumarin and a water miscible solvent, which non-competitive displacement agent separates any vitamin D metabolite in the sample from protein to which the vitamin D metabolite is bound, such that any separated vitamin D metabolite can be captured;
   (b) contacting the sample with a support having immobilised thereon a binding factor, which binding factor captures any vitamin D metabolite separated in step (a); and
   (c) measuring the amount of vitamin D metabolite captured in step (b).

4. The method of claim 3, wherein the vitamin D metabolite is 25-hydroxy vitamin D.

5. The method of claim 1 or claim 3, wherein the water miscible solvent is methanol.

6. The method of claims 1, 2 or 3, wherein the amount of vitamin D metabolite is measured in a binding assay.

7. The method of claim 6, wherein the binding assay is a competitive binding assay.

8. The method of claim 6, wherein the binding assay is an immunoassay.

9. The method of claim 7, wherein the competitive binding assay comprises the steps of:
   (a) providing a support having immobilized thereon a binding factor capable of binding a vitamin D metabolite;
   (b) contacting the support with a sample comprising the vitamin D metabolite to be measured and a non-competitive displacement agent comprising 8-anilino-1-napthalenesulfonic acid ammonium salt, 3-(acetonylbenzyl)-4-hydroxycoumarin and a water miscible solvent, which separates any vitamin D metabolite in the sample from protein to which the vitamin D metabolite is bound, so that any separated vitamin D metabolite binds to the binding factor;
   (c) contacting the support with a labeled form of the vitamin D metabolite; and
   (d) measuring the amount of labeled vitamin D metabolite left bound to the support,
wherein the amount of labeled vitamin D metabolite bound to the support is proportional to the amount of vitamin D metabolite in the sample.

10. The method of claim 9, wherein the binding factor immobilized on the support is vitamin D binding protein (DBP).

11. The method of claim 9, wherein the binding factor immobilized on the support is an anti-vitamin D metabolite antibody.

12. The method of claim 9, wherein the labeled vitamin D metabolite is labeled with biotin, avidin, a fluorescent molecule, or a chemiluminescent molecule.

* * * * *